(12) United States Patent
Nakayama et al.

(10) Patent No.: US 9,875,878 B2
(45) Date of Patent: Jan. 23, 2018

(54) SAMPLE HOLDER AND ANALYTICAL VACUUM DEVICE

(71) Applicant: HITACHI, LTD., Tokyo (JP)

(72) Inventors: Takeshi Nakayama, Tokyo (JP); Tomihiro Hashizume, Tokyo (JP); Akira Sugawara, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/038,879

(22) PCT Filed: Dec. 5, 2013

(86) PCT No.: PCT/JP2013/082708
§ 371 (c)(1),
(2) Date: May 24, 2016

(87) PCT Pub. No.: WO2015/083270
PCT Pub. Date: Jun. 11, 2015

(65) Prior Publication Data
US 2017/0004952 A1  Jan. 5, 2017

(51) Int. Cl.
*H01J 37/18* (2006.01)
*H01J 37/285* (2006.01)
(Continued)

(52) U.S. Cl.
CPC ........ *H01J 37/185* (2013.01); *G01N 23/2204* (2013.01); *H01J 37/20* (2013.01);
(Continued)

(58) Field of Classification Search
CPC ........ H01J 37/185; H01J 37/20; H01J 37/285; H01J 37/18; H01J 37/28
(Continued)

(56) References Cited

U.S. PATENT DOCUMENTS 6,608,317 B1 * 8/2003 Nakasuji ................ B82Y 10/00
   250/492.22
6,927,391 B2 * 8/2005 Tokuda ................ G01N 23/225
   250/307
(Continued)

FOREIGN PATENT DOCUMENTS

JP  2009-294235 A  12/2009
JP  2011-090973 A  5/2011

OTHER PUBLICATIONS

International Search Report of PCT/JP2013/082708 dated Feb. 18, 2014.

*Primary Examiner* — Nicole Ippolito
(74) *Attorney, Agent, or Firm* — Mattingly & Malur, PC

(57) ABSTRACT

Sample transferring can be securely and easily performed between an FIB device, an electron microscope, and an atom probe device, and atom probe analysis can be performed to a material that easily alters due to atmospheric exposure. A sample holder that holds a sample (12) is provided with an atmosphere-isolation mechanism that prevents the sample from altering due to the atmospheric exposure upon the sample transferring between the devices. There is provided a structure enabling of attaching and detaching a housing (21) of a sample holder leading end of a part of the atmosphere-isolation mechanism in an analytical vacuum device, such as the atom probe device.

9 Claims, 10 Drawing Sheets

(51) Int. Cl.
*H01J 37/20* (2006.01)
*G01N 23/22* (2006.01)

(52) U.S. Cl.
CPC ....... *H01J 37/285* (2013.01); *H01J 2237/184* (2013.01); *H01J 2237/204* (2013.01)

(58) Field of Classification Search
USPC .......... 250/306, 307, 309, 310, 311, 440.11, 250/441.11, 442.11, 443.1
See application file for complete search history.

(56) References Cited

U.S. PATENT DOCUMENTS

| | | | |
|---|---|---|---|
| 7,296,783 B2 * | 11/2007 | Kihara | ...................... F16K 3/18 251/193 |
| 2009/0218509 A1 * | 9/2009 | Ito | ........................... H01J 37/20 250/442.11 |
| 2012/0212583 A1 | 8/2012 | Yaguchi et al. | |
| 2015/0206705 A1 * | 7/2015 | Sakuma | .................. H01J 37/20 250/453.11 |

* cited by examiner

SAMPLE HOLDER AND ANALYTICAL VACUUM DEVICE

TECHNICAL FIELD

The present invention relates to a sample holder for a charged particle beam device, and an analytical vacuum device, such as an atom probe device, which analyzes a sample by using the sample holder.

BACKGROUND ART

Atom probe is an analytical method capable of directly observing atomic arrangement/composition distribution of a leading end of a sample that has been processed so as to be needle-shaped, at an atomic scale. In the atom probe, a high direct current voltage is applied so as to cause the leading end of the needle-shaped sample to generate a high electric field. A pulse voltage is applied or a pulse laser is irradiated to the leading end so that field evaporation of an atom belonging to a first layer of a surface is induced. Then, mass of an ion that has field-evaporated is time-of-flight-measured so that a type of an element can be determined. Since the field evaporation progresses every atomic layer, atom probe analysis has resolution in a depth direction at an atomic level (refer to PTL 1).

A peculiar high electric field in an order of $10^{10}$ (V/m) due to a metal is required in order to evaporate the metal by an electric field. In the atom probe analysis, a sample should be a needle-shaped sample having a leading end diameter of 100 nm or less in order to achieve the high electric field. In a case where a portion to be observed, such as a bulk sample, is uniformly present over an entire sample, an electric-field polishing method is used for processing of making a leading end of the sample to be acute. In contrast, since a region to be analyzed should be positioned at a leading end of a needle in order to perform the atom probe analysis to a specific region of a semiconductor, an interface, or the like, processing for a needle shape is performed using a focused ion beam (hereinafter, referred to as the "FIB").

Using the FIB enables easy processing of a sample in a needle-shape. However, only the FIB cannot often ascertain whether a leading end of the needle-shaped sample that has been completed actually includes a region to be analyzed. Thus, a sample that has been completed or a leading end of a needle-shaped sample that has been being processed, is sometimes observed by a transmission electron microscope (hereinafter, referred to as a "TEM"). In this case, processing and observation are alternately repeated in order to position a region to be analyzed at a leading end of a needle. Thus, a risk of damaging the sample increases. One holder is preferably shared and repeatedly used between the FIB and the TEM for purposes of a reduction of the risk that the sample is damaged and efficiency of work. PTL 2 describes a sample holder including an atmosphere-isolation mechanism that prevents a sample from altering by an atmospheric effect during a movement between an FIB and a TEM.

CITATION LIST

Patent Literatures

PTL 1: JP 2009-294235 A
PTL 2: JP 2011-090973 A

SUMMARY OF INVENTION

Technical Problem

When moving from a charged particle beam device, such as an FIB device or a TEM, to another element analysis device, since a needle-shaped sample processed for element analysis passes through an atmosphere, there is a risk that the needle-shaped sample reacts on a constituent in the atmosphere and alters depending on the material. Including a process of moving the needle-shaped sample to a specific holder of each of the measurement devices manually when the needle-shaped sample moves between different devices, causes a high risk that the sample is damaged/lost and time efficiency is degraded.

In atom probe analysis, a detector is disposed on an axis of the needle-shaped sample processed and an atom flies from a leading end of the needle-shaped sample to the detector so that measurement is performed. Thus, there is restriction that an ultra-high vacuum is maintained and a structure should not be present between the needle-shaped sample and the detector. Therefore, a structure that performs atmosphere-isolation and makes an airtight chamber around the sample, has been removed at a point in time at which the atom probe analysis is performed.

In order to solve the above problems, an object of the present invention is to provide a sample holder capable of preventing a needle-shaped sample from altering, by an atmosphere-isolation system, and also reducing a risk that the sample is damaged/lost, and an analytical vacuum device that performs analysis using the sample holder.

Solution to Problem

A sample holder according to the present invention includes a function that can be shared and introduced to vacuum devices, such as an FIB device, a TEM, and an atom probe device, includes an atmosphere-isolation mechanism that prevents a sample from altering due to atmospheric exposure upon sample transferring between the individual measurement devices, and includes a structure that can attach and detach a housing of a sample holder leading end of a part of the atmosphere-isolation mechanism in the analytical vacuum device, such as the atom probe device.

That is, the sample holder according to the present invention includes: a cylindrical body including one end open; a sample base including a sample holding portion that holds a sample, at a leading end; a drive support portion coupling to the sample base so as to be attachable and detachable, and configured to be movable in the body; and a housing including a vacuum seal portion and an opening through which a charged particle beam to be irradiated to the sample held by the sample holding portion passes, enveloping the sample holding portion of the sample base at least partially, and coupling to the sample base or the drive support portion so as to be attachable and detachable. In a state where the drive support portion, the sample base, and the housing have been coupled to each other, the drive support portion is introduced into the body so that the vacuum seal portion of the housing comes in contact with the body and an airtight chamber is formed on a periphery of the sample holding portion.

The coupling manner between the sample base and the drive support portion and a coupling manner between the housing and the sample base or the drive support portion are different from each other.

For example, the housing may be attachable to and detachable from the sample base by rotation motion around an axis of the sample holder.

For example, the housing may be attachable to and detachable from the drive support portion by rotation motion around the axis of the sample holder.

The sample base may include an external cylinder and an internal cylinder that has the sample holding portion on the leading end and is axially rotatable inside the external cylinder. The sample holder may include a rotating mechanism for axially rotating the internal cylinder with respect to the external cylinder.

The analytical vacuum device according to the present invention includes a mechanism that can securely and easily attach and detach a housing of a sample holder leading end in an element analysis device, and includes a mechanism that fixes the sample base to a sample fixing portion at an analyzing position in an analyzing chamber.

That is, the analytical vacuum device according to the present invention includes a sample fixing portion configured to fix a sample base that has held a sample in a vacuum chamber, and analyzes the sample that has been held by the sample base. The analytical vacuum device includes: an attaching and detaching mechanism configured to separate three being the housing, the sample base, and the drive support portion included in the body from the sample holder according to the present invention, and configured to couple the three to the sample holder, in the vacuum chamber; and a mechanism configured to transfer and fix the sample base that has been separated, to the sample fixing portion.

For example, the attaching and detaching mechanism includes a mechanism that separates the housing and the sample base.

For example, the attaching and detaching mechanism includes a mechanism that separates the housing from the drive support portion.

Advantageous Effects of Invention

Using a sample holder and an analytical vacuum device according to the present invention enables performing elemental analysis to a material that easily alters due to atmospheric exposure. In addition, sample transferring can be secure and easy between an FIB device, a scanning electron microscope (SEM), a TEM, and an analysis device such as atom probe, from needle-shaped sample processing to measurement.

Problems, configurations, and effects other than the above descriptions will be clarified by the following embodiments.

DESCRIPTION OF EMBODIMENTS

Embodiments of the present invention will be described in detail below using the drawings.

First Embodiment

Figure 4:
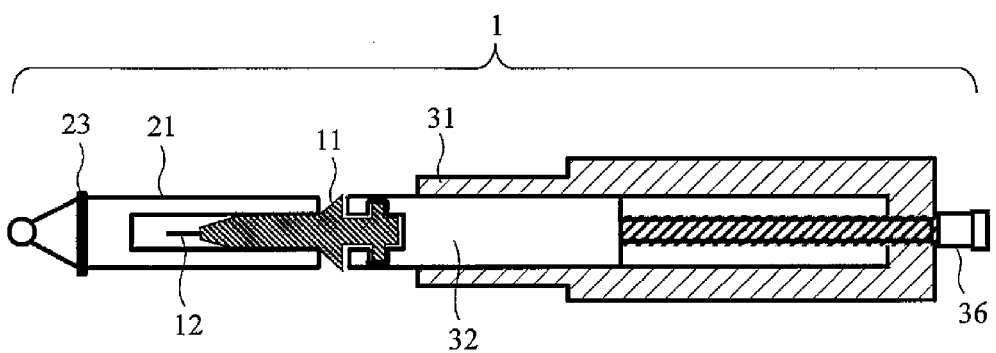
FIG. 4 is a cross-sectional schematic view of the entire sample holder disposed in an atmosphere-opening state.

FIG. 4 is a cross-sectional schematic view of a structure of an entire sample holder 1 according to a first embodiment of the present invention. The sample holder 1 includes four parts: a sample base 11, a housing 21, a cylindrical body 31 having one end open, and a drive support portion 32 capable of translational motion inside the cylindrical body 31. By operating a micrometer 36, the drive support portion 32 is translated in a direction in which the drive support portion 32 protrudes from the cylindrical body 31 or in a direction in which the drive support portion 32 is introduced to the inside of the cylindrical body 31. The housing 21 and the sample base 11 include structures that couple to each other so as to be attachable and detachable. The sample base 11 and the drive support portion 32 include structures that couple to each other so as to be attachable and detachable. The sample base 11 holds a needle-shaped sample 12. The housing 21 has a substantially U-shaped frame shape, and includes an O-ring 23 as a vacuum seal member disposed on the side opposite to the side on which the sample base 11 is attached and detached.

Figure 1:
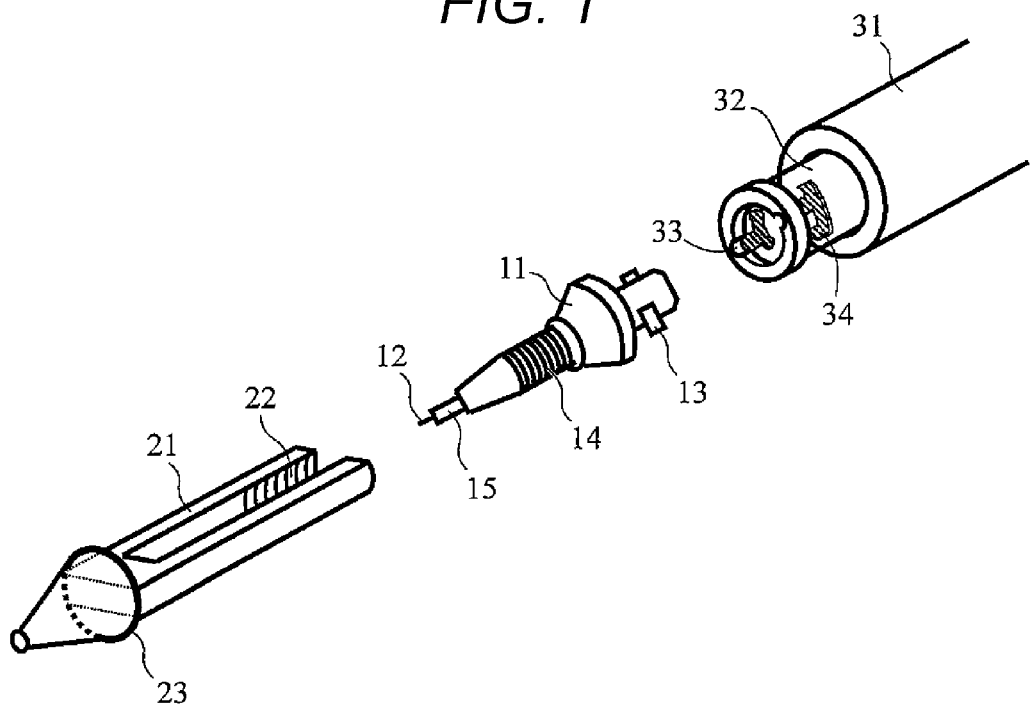
FIG. 1 is an exploded perspective view of a leading end of an exemplary sample holder according to the present invention.

FIG. 1 is an exploded perspective view of a leading end of the sample holder 1 according to the first embodiment of the present invention. The needle-shaped sample 12 is held by a sample holding portion 15 positioned at a leading end part of the sample base 11. The sample base 11 has, for example, a male screw structure 14 on an outer surface. The housing 21 has a female screw structure 22 on an inner surface on the side on which the sample base 11 is attached and detached. The sample base 11 and the housing 21 are coupled to each other so as to be attachable and detachable in a "rotation" manner due to the male screw and the female screw. Meanwhile, the sample base 11 and the drive support portion 32 are coupled to each other so as to be attachable and detachable in a "translation+rotation" manner. A tail end portion of the sample base 11 includes, for example, two protrusions 13 disposed thereon. The drive support portion 32 has a cylindrical leading end portion into which the tail end portion of the sample base 11 is inserted. A pair of L-shaped guide grooves 33 that correspond to the two protrusions 13 disposed on the sample base 11, is disposed on a cylindrical inner wall. The sample base 11 and the drive support portion 32 have the following bayonet-typed coupling structures. The protrusions 13 move along the pair of guide grooves 33 disposed on the cylindrical inner wall of the drive support portion 32 so that the tail end portion of the sample base 11 is inserted into the leading end portion of the drive support portion 32. After that, the drive support portion 32 rotates around a holder axis so that the protrusions 13 are hooked and fixed in hook portions 34 at leading ends of the L-shaped guide grooves.

Here, the two different coupling manners: the "rotation" and the "translation+rotation" are used for the connection between the sample base 11 and the housing 21, and the connection between the sample base 11 and the drive support portion 32, respectively. Therefore, the selective separation and connection can be performed in a vacuum chamber. Three types: "rotation", "translation", and "rotation+translation" can be applied to a coupling manner between the sample base 11 and the housing 21 and a coupling manner between the sample base 11 and the drive support portion 32. Any of the three types may be used to the coupling manner between the sample base 11 and the housing 21 and the coupling manner between the sample base 11 and the drive support portion 32 if the coupling manners are different from each other. Note that, the structure in which the housing 21 is coupled to the sample base 11, has been illustrated in FIG. 1. The housing 21 may be coupled to the drive support portion 32, and the example will be described in a second embodiment.

Figure 2:
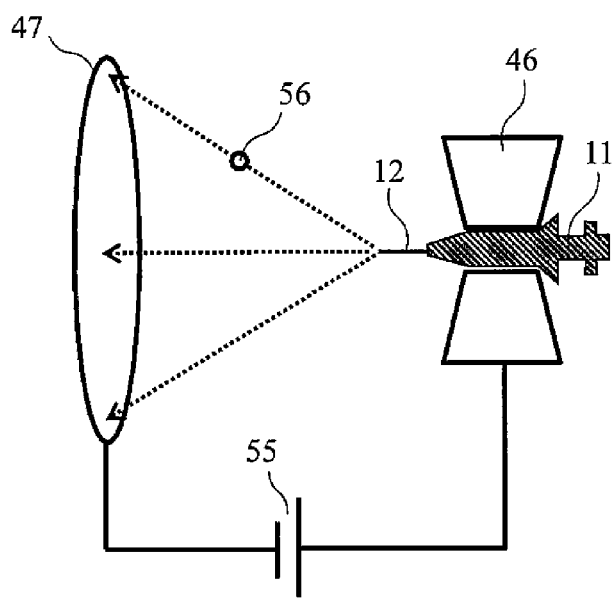
FIG. 2 is a schematic view of a configuration of atom probe analysis.

FIG. 2 is a schematic view of a configuration when three-dimensional atom probe analysis is performed as an example of separating the sample base 11 from the sample holder 1 and using the sample base 11 independently. The sample base 11 that holds the needle-shaped sample 12 is separated and transferred from the sample holder 1 illustrated in FIG. 1. The sample base 11 is set to a sample fixing portion 46 for the atom analysis in an atom probe device. Then, the three-dimensional atom probe analysis can be performed. In the three-dimensional atom probe analysis, a high voltage is applied across the needle-shaped sample 12 and a detector 47 by using a voltage source 55. Then, an electric field focuses on the leading end of the needle-shaped sample 12 held by the sample base 11. After that, an atom 56 radially field-evaporated from the leading end of the sample is detected by the detector 47 so that the measurement is performed. Accordingly, a structure, such as the housing 21, should not be present between the needle-shaped sample 12 and the detector 47.

Figure 3:
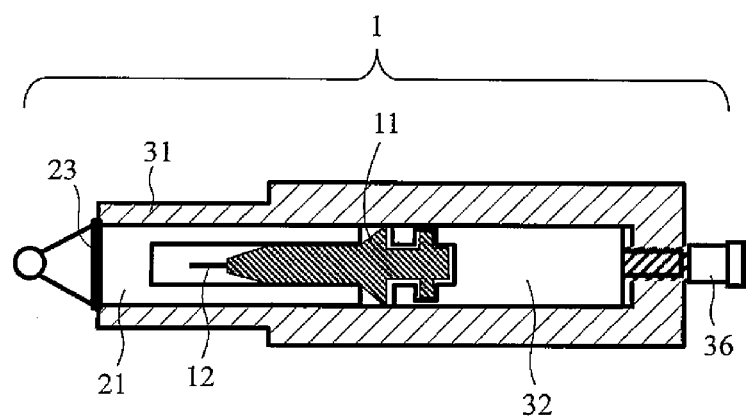
FIG. 3 is a cross-sectional schematic view of the entire sample holder disposed in an atmosphere-isolation state.

Meanwhile, the housing 21 is a constituent element necessary for making an atmosphere-isolation state in the sample holder 1. FIG. 3 is a cross-sectional schematic view of the entire sample holder 1 disposed in the atmosphere-isolation state. In the atmosphere-isolation state, the entirety of the housing 21, the sample base 11, and the drive support portion 32, has been introduced into the cylindrical body 31 in a state where the housing 21 has been coupled to the sample base 11 and the sample base 11 has been coupled to the drive support portion 32. The O-ring 23 for a vacuum seal disposed on the housing 21 comes in contact with an inner wall of the cylindrical body 31 so that an airtight chamber is formed around the needle-shaped sample 12 held by the sample base 11. When the atom probe analysis is performed, a structure should not be present ahead of the needle-shaped sample 12. However, the housing 21 including a vacuum seal member, such as the above O-ring 23, is required in order to make the airtight chamber around the needle-shaped sample 12.

As described later in FIG. 7, when the sample holder is unloaded from a vacuum device, such as an FIB device, a TEM, and the atom probe device, the leading end of the sample holder is made to be in the atmosphere-isolation state before being exposed to an atmosphere. Airtightness around the needle-shaped sample 12 is retained so that the sample 12 is prevented from being exposed to oxygen or moisture in the atmosphere upon the sample transferring in the atmosphere between the vacuum devices. As described above, a separating mechanism as illustrated in FIG. 1 is required in order to share and use the sample base 11 between the atom probe device and a charged particle beam device.

FIG. 4 is a cross-sectional schematic view of the entire sample holder disposed in an atmosphere-opening state. When the micrometer 36 is operated, the drive support portion 32 and an entire structure coupled to the drive support portion 32 are translated in an axial direction of the sample holder. Then, the O-ring 23 disposed on the housing 21 comes in contact with the inner wall of the cylindrical body 31 and a space in which the needle-shaped sample 12 has been held is sealed. Therefore, the atmosphere-isolation state as illustrated in FIG. 3 can be made. Only operating the micrometer 36 can change the atmosphere-isolation state to the atmosphere-opening state and vice versa. The atmosphere-opening state is mainly used (1) when the sample is attached/detached in the atmosphere, (2) when processing/observation are performed in the charged particle beam device, and (3) when the sample base is transferred in the atom probe device.

Figure 5:
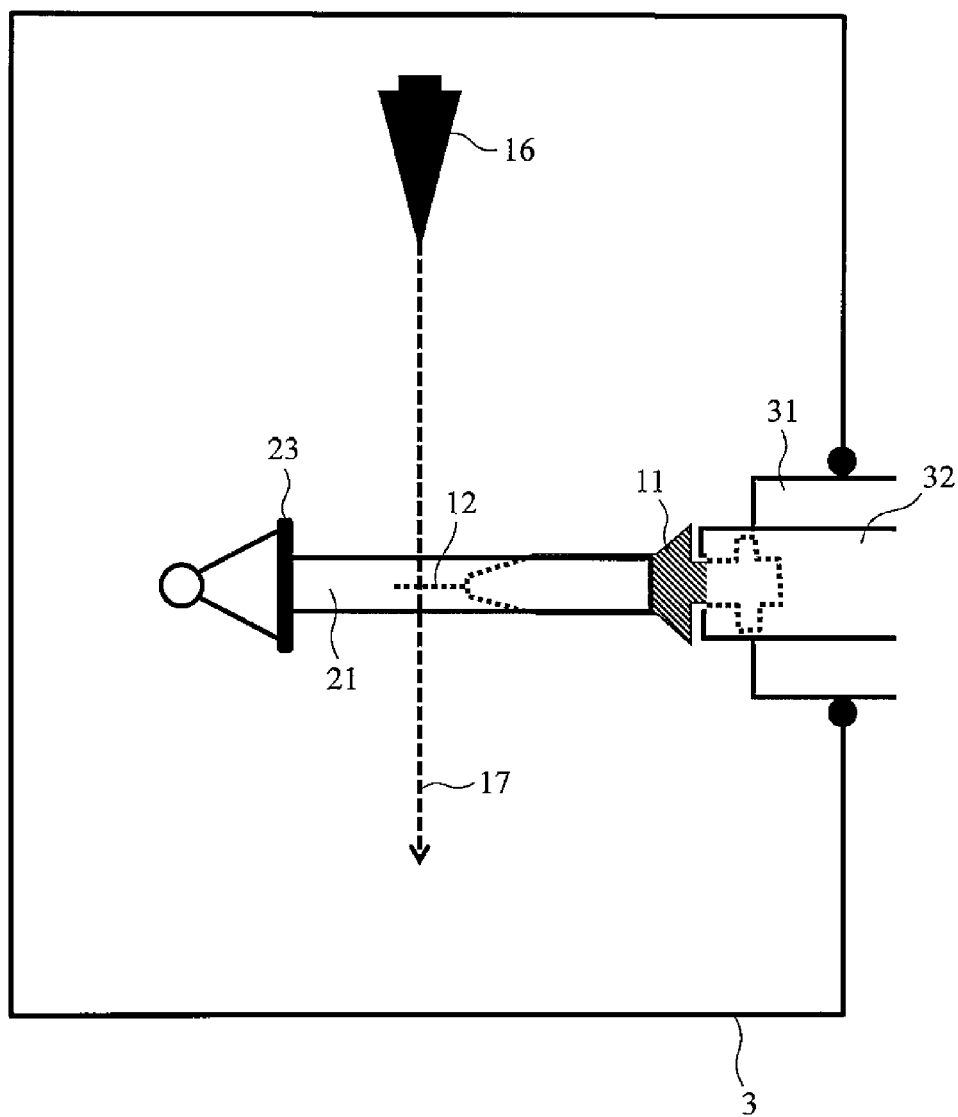
FIG. 5 is a schematic view of the sample holder when processing/observation are performed in a charged particle beam device.

FIG. 5 is a schematic view of the sample holder 1 when the processing/observation are performed in the charged particle beam device 3. The leading end of the sample holder 1 is in the atmosphere-opening state so that a charged particle beam 17 emitted from a charged particle beam source 16 can be perpendicularly incident on and transmitted to the needle-shaped sample 12 through an opening of the housing 21. Processing of the needle-shaped sample 12 by an FIB and observation by an electron microscope (TEM/SEM) are performed in the atmosphere-opening state by integrating the housing 21, the sample base 11, and the drive support portion 32, as illustrated in FIG. 5. When the processing/observation have been completed and the sample is transferred to the following device, the atmosphere-isolation state should be made before the sample holder 1 is unloaded, and the airtightness around the needle-shaped sample 12 is made to be retained outside the vacuum device. At a stage of preparing a needle-shaped sample for atom probe analysis, FIB processing and TEM observation are sometimes repeatedly performed so that a leading end of the needle-shaped sample that has been prepared includes a region to be analyzed. Thus, when the sample is transferred between the devices, it is important that the sample holder should be in the atmosphere-isolation state and an effect of atmospheric exposure is minimized.

Figure 6:
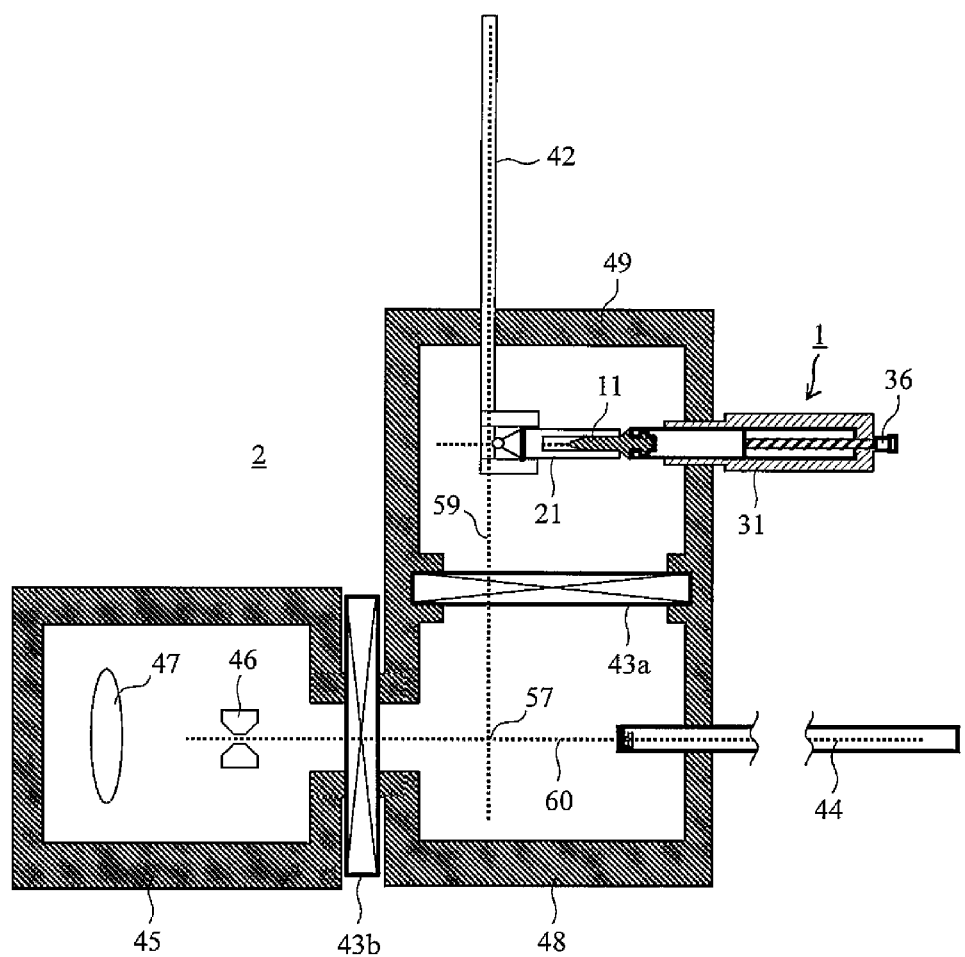
FIG. 6 is a schematic view of an exemplary atom probe device including a housing attaching and detaching mechanism.

FIG. 6 is a schematic view of an exemplary atom probe device including a housing attaching and detaching mechanism. When atom probe analysis is performed, the housing 21 coupled to the sample base 11 attachable and detachable so as to partially envelop the needle-shaped sample 12 held by the sample holding portion 15 of the sample base 11, is required to be securely detached in a vacuum and only the sample base 11 is required to move to the sample fixing portion 46 for the atom probe analysis. Thus, a housing attaching and detaching mechanism for the sample holder is required. The atom probe device 2 illustrated in FIG. 6 includes three chambers: a preliminary discharging chamber 49, a sample exchanging chamber 48, and an atom probe analyzing chamber 45. A viewport has been mounted on each of the chambers so that whether the housing 21 has been securely and certainly being attached to and detached from the sample holder 1 can be visually ascertained. The atom probe device illustrated in FIG. 6 includes a housing holder 42 capable of pinching, holding, and moving the housing to a predetermined position as the housing attaching and detaching mechanism. The atom probe device also includes a sample exchanging rod 44 as a mechanism capable of detaching the sample base from the sample base 11 and the housing 21 that have been separated from the drive support portion 32 and held by the housing holder 42, and moving the sample base to the sample fixing portion 46 for the atom probe analysis.

Figure 7:
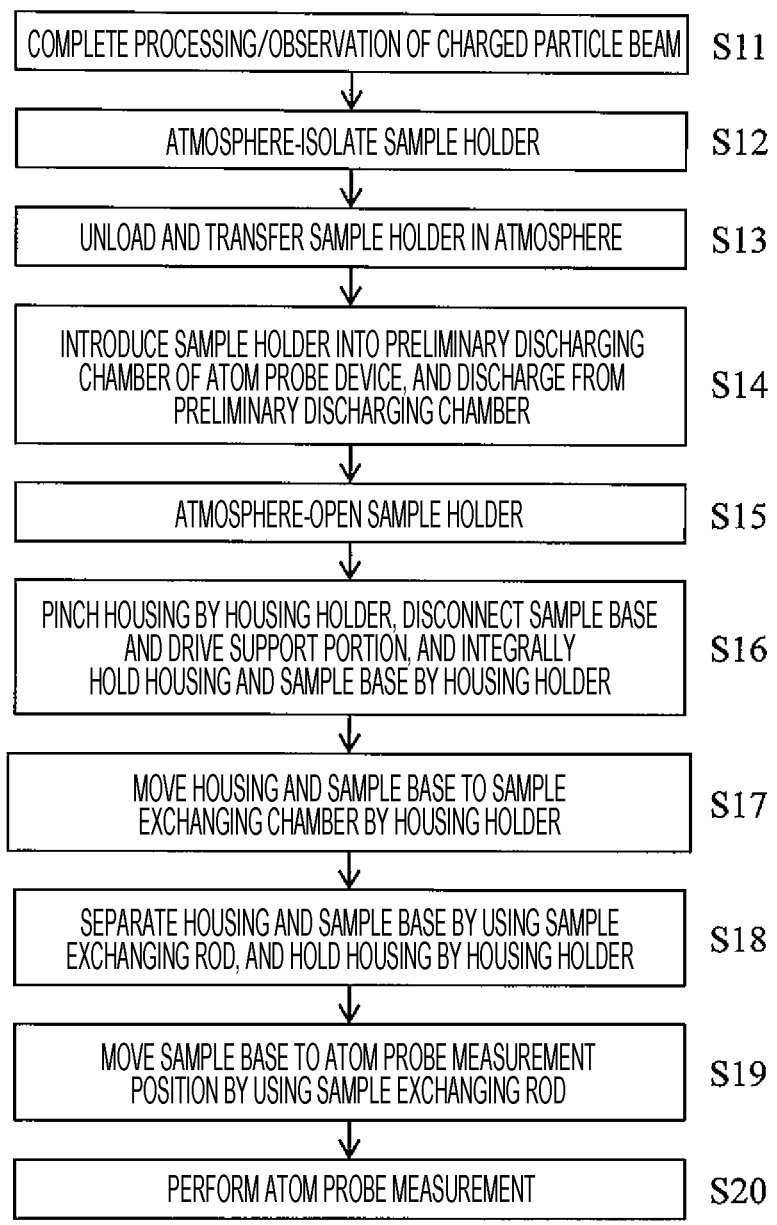
FIG. 7 is a flow chart of operations from charged particle beam processing/observation to the atom probe analysis.

FIG. 7 is a flow chart of operational processes, with respect to the sample holder 1, for transferring the sample with which charged particle beam observation has been completed, from the charged particle beam device to the sample fixing portion 46 for measurement of the atom probe device, without atmospheric exposure.

At Step 11, the processing/observation have been completed in the charged particle beam device illustrated in FIG. 5. At Step 12, the sample holder is made to be in the atmosphere-isolation state in a vacuum chamber of the charged particle beam device for preparation for moving the sample holder in the atmosphere. After that, at Step 13, the sample holder is unloaded from the charged particle beam device. The entire sample holder that has been retained in the atmosphere-isolation state, is transferred to the atom probe device in the atmosphere. Next, at Step 14, the sample holder is introduced to the preliminary discharging chamber 49 of the atom probe device 2 illustrated in FIG. 6, and then discharging of the preliminary discharging chamber 49 starts. When the degree of vacuum increases in the preliminary discharging chamber 49, the processing proceeds to Step 15. The micrometer 36 of the sample holder is turned so that the sample holder made to be in the atmosphere-opening state.

Figure 8:
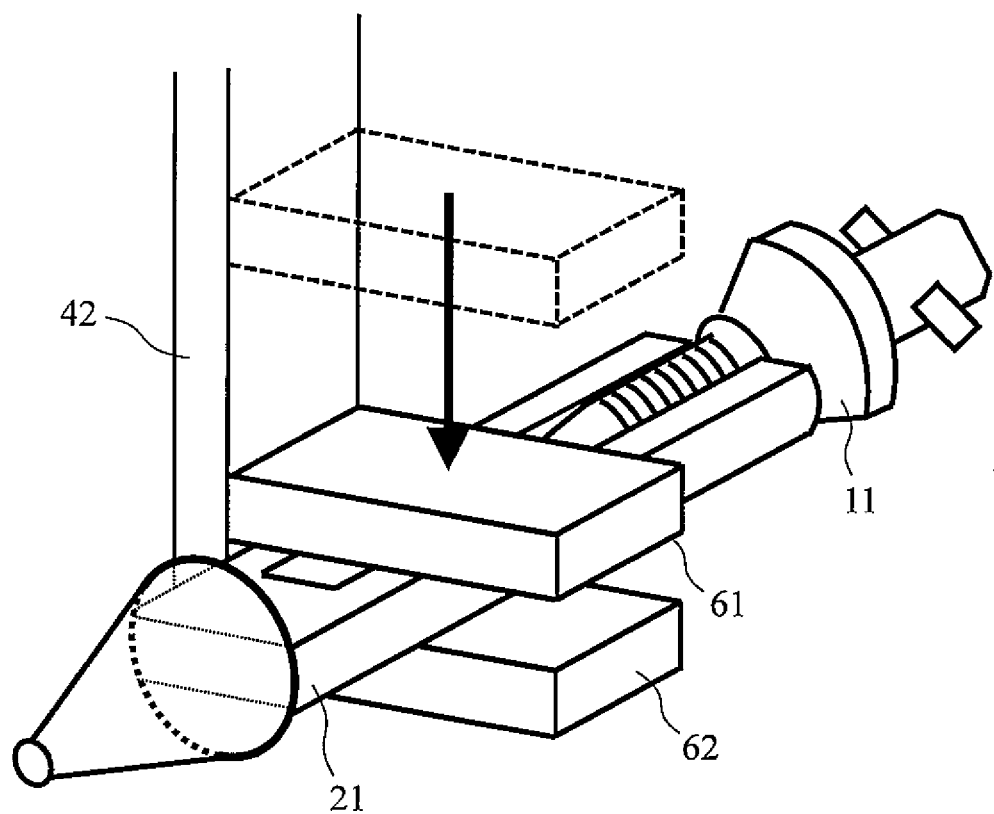
FIG. 8 is a schematic perspective view illustrating a state where a housing holder has retained the housing.

Next, at Step 16, the housing holder 42 is used so as to pinch and fix the housing 21 of the sample holder. After that, the entire sample holder is made to be in motion of a combination of rotation and translation so that the protrusions 13 of the sample base 11 are released from the hook portions 34 at the leading ends of the L-shaped guide grooves 33 of the drive support portion 32, and the drive support portion 32 and the sample base 11 are separated from each other. At this point in time, as illustrated in FIG. 8, the housing 21 and the sample base 11 have been held by only the housing holder 42 in a state where the housing 21 and the sample base 11 have been coupled in the preliminary discharging chamber 49. The exemplary housing holder 42 illustrated in the drawing has a structure in which an upper plate 61 is movable with respect to a lower plate 62 that has been fixed. The housing holder 42 interposes and holds a flat portion of the housing 21 between the lower plate 62 and the upper plate 61. Here, a leading end structure of the housing holder 42 may be a structure capable of coming in contact with only the housing 21 and securely holding the housing 21 in a vacuum so as to prevent the housing 21 from rotating with the needle-shaped sample 12 in a coaxial direction. The configuration is not limited to that illustrated in the drawing.

Next, a gate valve 43*a* opens between the preliminary discharging chamber 49 and the sample exchanging chamber 48. At Step 17, the housing holder 42 operates so as to move the sample base 11 and the housing 21 to a drawing position 57 that is an intersection of a movement axis 59 of the housing holder (refer to FIG. 6) and a movement axis 60 of the sample exchanging rod 44, in the sample exchanging chamber 48. At Step 18, the sample exchanging rod 44 rotates the sample base 11 in a state where the housing holder 42 has fixed the housing 21, so as to draw the sample base 11 from the housing 21. At this point in time, the housing 21 has been held by the housing holder 42 and the sample base 11 has been held by the sample exchanging rod 44. Thus, the housing holder 42 operates so that the housing 21 moves in a direction except the axial direction of the needle-shaped sample 12 and can be held at an evacuating position. Note that, a coupling manner between the sample base 11 and the sample exchanging rod 44 is made to be similar to the coupling manner between the sample base 11 and the drive support portion 32 so that the structure can be simple.

At Step 19 to be continued, a gate valve 43*b* opens between the sample exchanging chamber 48 and the atom probe analyzing chamber 45. The sample exchanging rod 44 moves the sample base 11 to the sample fixing portion 46 for the atom probe analysis. In this case, the coupling manner between the sample base 11 and the sample fixing portion 46 for the atom probe analysis is made to be similar to the coupling manner between the sample base 11 and the housing 21 so that the structure can be simple. Since cooling efficiency of the sample increases in the atom probe analysis, it is advantageous that the coupling manner between the sample base 11 and the sample fixing portion 46 for the atom probe analysis is made to have, for example, a screw structure that increases a contact area. The coupling manner is not necessarily limited to the screw structure. Next, at Step 20, after the sample base 11 is fixed to the sample fixing portion 46 for the atom probe analysis, the sample exchanging rod 44 is detached from the sample base 11, resulting in a state similar to that in FIG. 2. After that, the sample exchanging rod 44 is evacuated and the gate valve 43*b* closes. Then, the atom probe analysis is performed.

By this series of processes, the sample base 11 built in the sample holder 1 can be transferred to the sample fixing portion 46 for the atom probe analysis in the atom probe device 2 without atmospheric exposure. Note that, in the example in FIG. 6, the atom probe device includes the three chambers: the preliminary discharging chamber 49, the sample exchanging chamber 48, and the atom probe analyzing chamber 45. For example, a two-chamber configuration including the housing holder 42 and the sample exchanging rod 44 disposed in the common sample exchanging chamber 48, can be also applied. The configuration is not limited to this.

Second Embodiment

Figure 9:
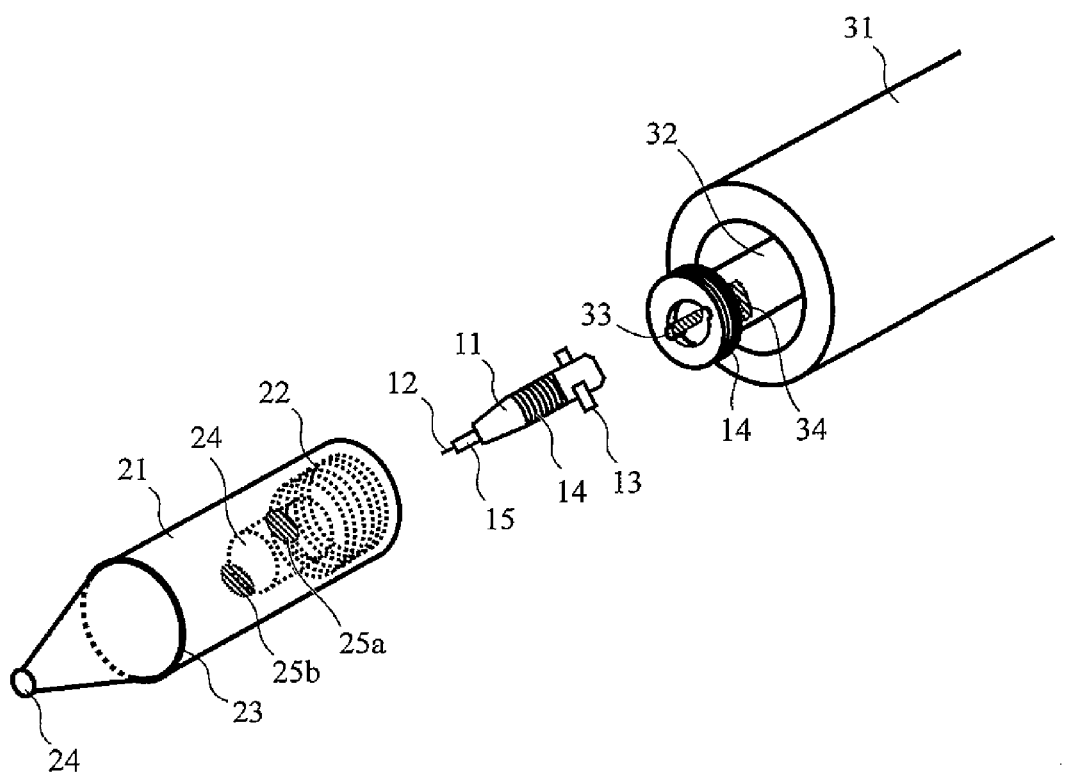
FIG. 9 is an exploded perspective view of a leading end of another exemplary sample holder according to the present invention.

FIG. 9 is an exploded perspective view of a structure of a sample holder leading end according to a second embodiment of the present invention. A leading end portion of the sample holder includes four members: a sample base 11, a housing 21, a cylindrical body 31, and a drive support portion 32. According to the second embodiment, the housing 21 is coupled to the drive support portion 32 in a "rotation" manner and the sample base 11 is coupled to the drive support portion 32 in a "translation+rotation" manner.

As illustrated in FIG. 9, a leading end portion of the drive support portion 32 has a male screw structure 14 on an outer surface. The housing 21 has a female screw structure 22 on an inner surface. The housing 21 and the drive support portion 32 have the structures so as to be coupled to each other by rotation around a holder axis. The leading end portion of the drive support portion 32 has a cylindrical recess portion into which a tail end portion of the sample base 11 can be inserted. An inner wall of the recess portion includes a pair of L-shaped guide grooves 33 disposed thereon. A tail end portion of the sample base 11 includes, for example, two protrusions 13 disposed thereon. The sample base 11 and the drive support portion 32 have the following bayonet-typed coupling structures. The protrusions 13 move along the pair of guide grooves 33 disposed on the inner wall of the recess portion of the drive support portion 32 so that the tail end portion of the sample base 11 is inserted into the leading end portion of the drive support portion 32. After that, the drive support portion 32 rotates around the holder axis so that the protrusions 13 are hooked and fixed in hook portions 34 at leading ends of the L-shaped guide grooves. As described above, a coupling manner between the drive support portion 32 and the housing 21 and a coupling manner between the sample base 11 and the drive support portion 32 are made to be different from each other. Thus, the selective separation and connection can be performed in a vacuum chamber. The housing 21 has a space 24 housing a sample base 11 and a needle-shaped sample 12 held by a sample holding portion 15 of the sample base 11, inside. The space 24 communicates with the exterior through a pair of holes 25a and 25b disposed on a side portion of the housing. The pair of holes 25a and 25b serves to pass an ion beam or an electron beam to be irradiated to the needle-shaped sample 12 that has been covered by the housing 21 and held in an atmosphere-opening state in a charged particle beam device, such as an FIB device or a TEM, through.

Figure 10:
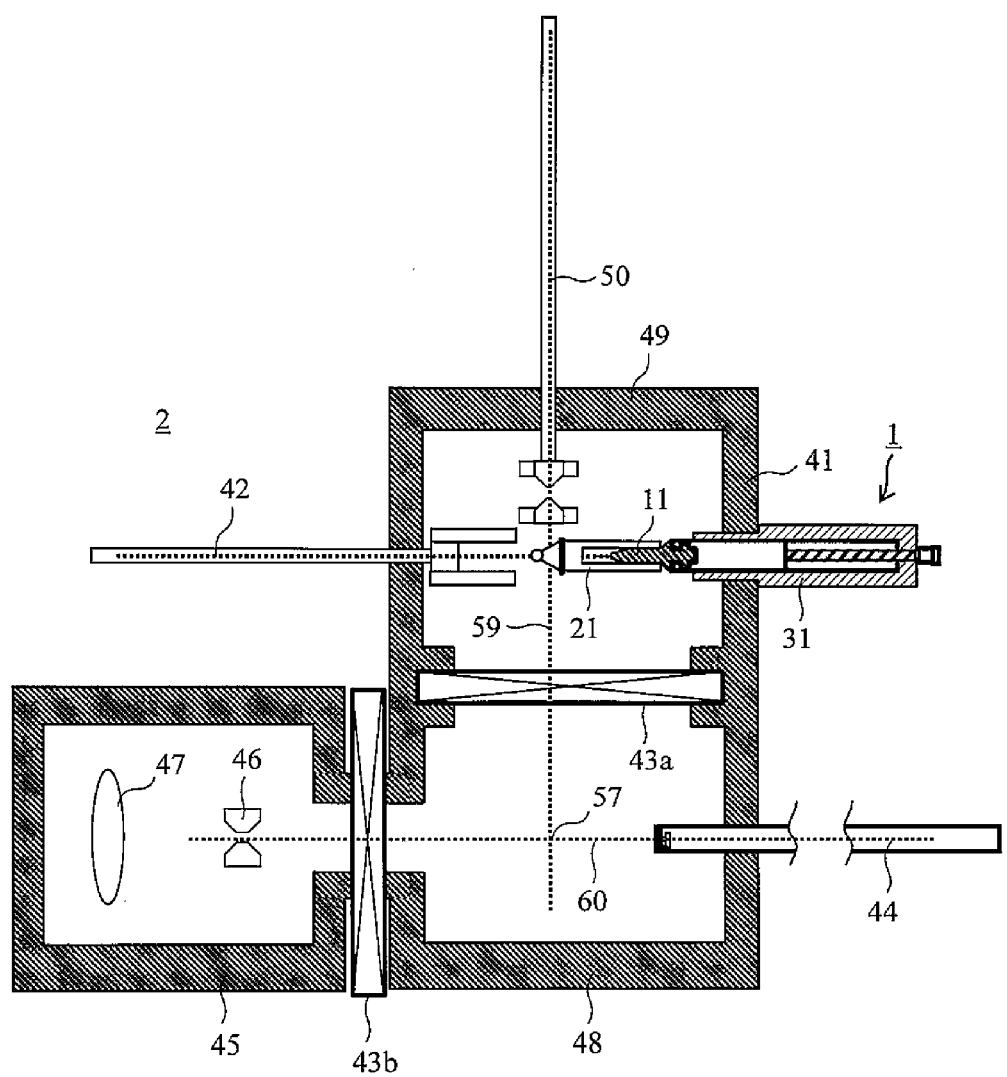
FIG. 10 is a schematic view of an exemplary atom probe device including a housing attaching and detaching mechanism.

FIG. 10 is a schematic view of an exemplary atom probe device including a housing attaching and detaching mechanism. Similarly to the first embodiment, when atom probe analysis is performed, the housing 21 held by the sample base 11 and positioned at a leading end of the needle-shaped sample 12 is required to be securely detached in a vacuum. It is necessary to move only the sample base 11 to a sample fixing portion 46 for the atom probe analysis. According to the second embodiment, the housing 21 is detached in a preliminary discharging chamber 49. There is no problem that even the housing 21 is detached anywhere as long as the housing 21 can be reversibly attached and detached. The configuration is not limited to this. The example illustrated in FIG. 10 includes, as an attaching and detaching mechanism of the housing 21, a housing holder 42 capable of pinching and fixing the housing. In addition, a sample introducing rod 50 is included as a mechanism for separating the sample base 11 that has been exposed by detaching the housing 21, from the drive support portion 32 of the sample holder. Furthermore, a sample exchanging rod 44 is included as a mechanism for receiving the sample base 11 from the sample introducing rod 50 and fixing the sample base 11 to the sample fixing portion 46.

Figure 11:
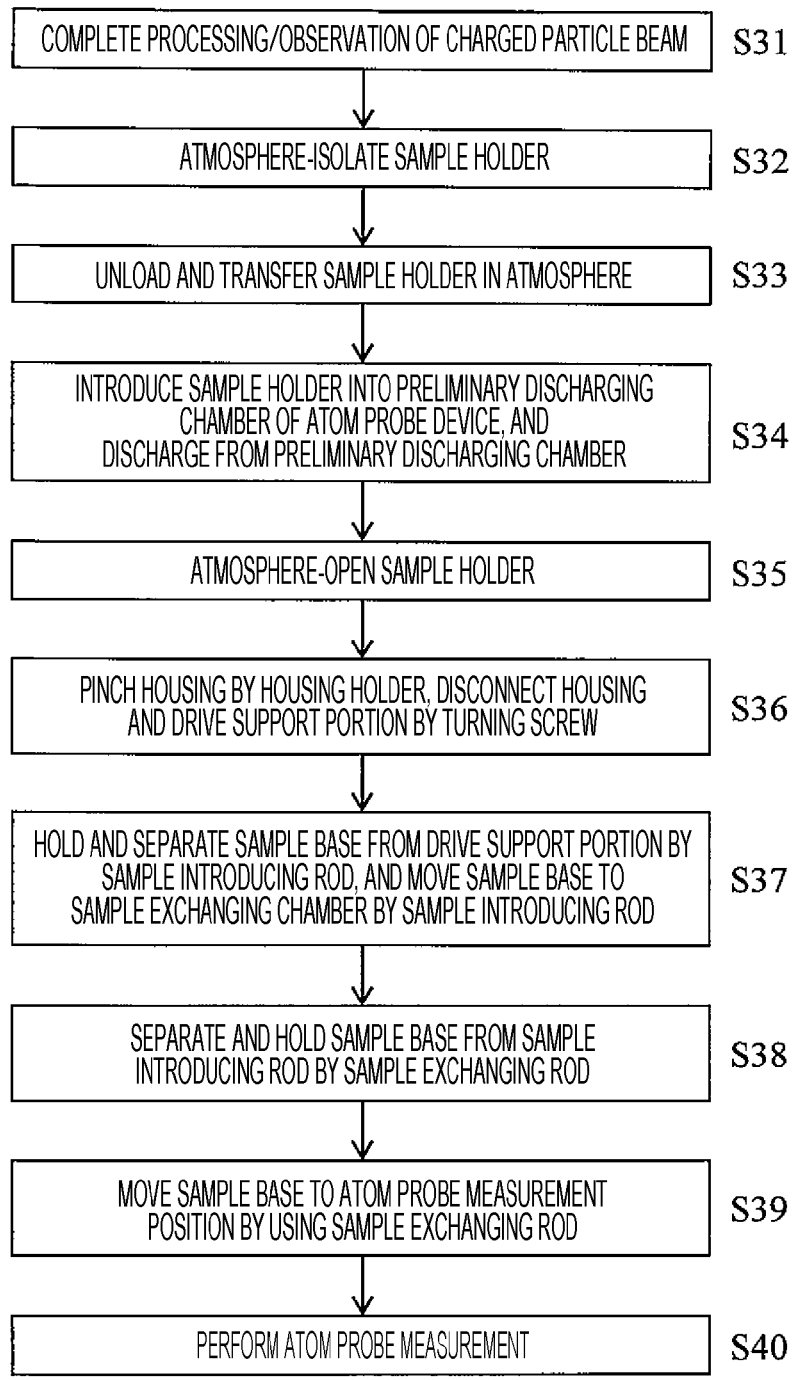
FIG. 11 is a flow chart of operations from charged particle beam processing/observation to atom probe analysis.

FIG. 11 is a flow chart of operational processes, with respect to the sample holder 1, for transferring the sample with which charged particle beam observation has been completed, to the sample fixing portion 46 for the atom probe analysis, without atmospheric exposure.

At Step 31, processing/observation have been completed in the charged particle beam device illustrated in FIG. 5. At Step 32, the sample holder is made to be in an atmosphere-isolation state in a vacuum chamber of the charged particle beam device for preparation for moving the sample holder in an atmosphere. After that, at Step 33, the sample holder is unloaded from the charged particle beam device. The entire sample holder that has been retained in the atmosphere-isolation state, is transferred to the atom probe device in the atmosphere. Next, at Step 34, the sample holder is introduced to the preliminary discharging chamber 49 of the atom probe device 2 illustrated in FIG. 10, and then discharging of the preliminary discharging chamber 49 starts. When the degree of vacuum increases in the preliminary discharging chamber 49, the processing proceeds to Step 35. A micrometer 36 of the sample holder 1 is turned so that the sample holder 1 is made to be in the atmosphere-opening state.

Next, at Step 36, the housing holder 42 is used so as to pinch and fix the housing 21. Then, the housing holder 42 rotates so that the housing 21 is unloaded from drive support portion 32. At this point in time, the sample base 11 has been held by the sample holder 1 in the preliminary discharging chamber 49 and the housing 21 has been held by the housing holder 42 in a state where the sample base 11 has been coupled to the drive support portion 32. The housing holder 42 that has held the housing 21 is evacuated to a position that does not prevent an operation to be performed thereafter.

Next, a gate valve 43a opens between the preliminary discharging chamber 49 and a sample exchanging chamber 48. At Step 37, the sample introducing rod 50 separates the sample base 11 from the drive support portion 32. The sample introducing rod 50 thrusts so that the sample base 11 moves to the sample exchanging chamber 48. The sample introducing rod 50 has a female screw structure that engages with a male screw structure disposed on the sample base 11. Upon the separation of the sample base 11 from the drive support portion 32, rotating the entire sample holder around the axis screw-joins and fixes the sample base 11 to the sample introducing rod 50. After that, the entire sample holder is made to be in motion of a combination of rotation and translation. Then, the protrusions 13 of the sample base 11 are released from the hook portions 34 at the leading ends of the L-shaped guide grooves 33 of the drive support portion 32 so that the sample base 11 is separated.

Next, at Step 38, the sample exchanging rod 44 separates/holds the sample base 11 from the sample introducing rod 50. The sample exchanging rod 44 includes a bayonet-typed coupling structure similar to that of the drive support portion 32, at a leading end thereof. Next, a gate valve 43b opens between the sample exchanging chamber 48 and an atom probe analyzing chamber 45. The processing proceeds to Step 39. The sample exchanging rod 44 moves the sample base 11 to the sample fixing portion 46 for the atom probe analysis. Subsequently, the processing proceeds to Step 40. After the sample base 11 has been fixed to the sample fixing portion 46 for the atom probe analysis, the sample exchanging rod 44 is detached from the sample base 11, resulting in a state similar to that in FIG. 2. After that, the sample exchanging rod 44 is evacuated and the gate valve 43b closes. Then, the atom probe analysis is performed.

By this series of processes, the sample transferring can be performed without the atmospheric exposure from the processing/observation to a stage at which the atom probe analysis is performed. Note that, in the example in FIG. 10, the atom probe device 2 includes the three chambers: the preliminary discharging chamber 49, the sample exchanging chamber 48, and the atom probe analyzing chamber 45. For example, a two-chamber configuration including the housing holder 42 and the sample exchanging rod 44 disposed in the common sample exchanging chamber 48, can be applied. The configuration is not limited to this.

Third Embodiment

Figure 12:
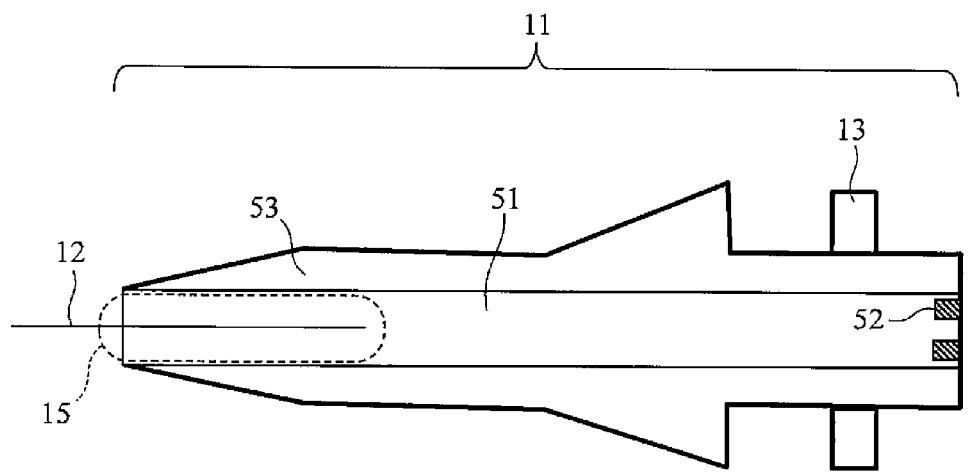
FIG. 12 is a cross-sectional schematic view of a structure of a sample base having a sample rotating mechanism.

FIG. 12 is a cross-sectional schematic view of a structure of a sample base 11 having a sample rotating mechanism according to a third embodiment of the present invention.

The sample base 11 according to the present embodiment includes an external cylinder 53 and a rotary internal cylinder 51. The external cylinder 53 includes a protrusion 13 disposed thereon. The rotary internal cylinder 51 has a sample holding portion 15 at a leading end thereof. A needle-shaped sample 12 can be fixed to the rotary internal cylinder 51. A groove 52 at a tail end of the rotary internal cylinder 51 is used and axial rotation of the rotary internal cylinder 51 is performed with respect to the external cylinder 53 of the sample base 11. Thus, axial rotation of the needle-shaped sample 12 can be performed. Accordingly, an incident direction of a charged particle beam with respect to the needle-shaped sample 12 can be changed. Note that, the groove 52 that rotates the rotary internal cylinder 51, may be replaced to another structure. For example, a protrudent structure may be applied.

Figure 13:
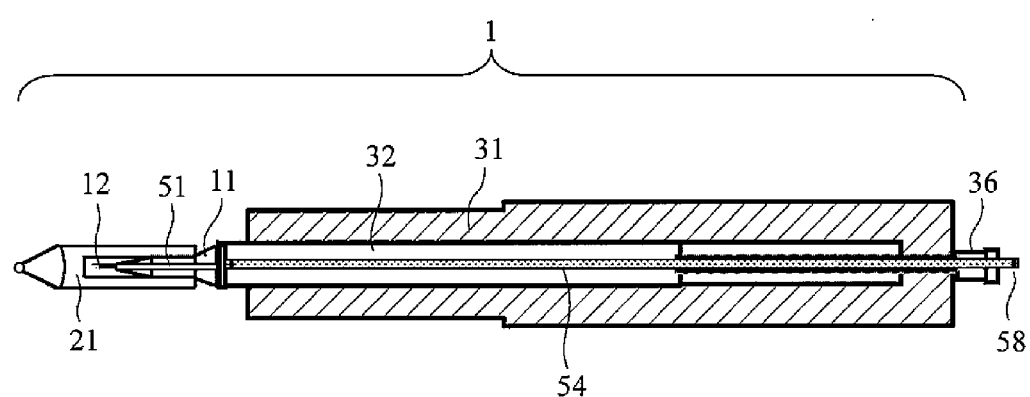
FIG. 13 is a cross-sectional schematic view of a structure of an entire sample holder having the sample rotating mechanism.

FIG. 13 is a cross-sectional schematic view of an entire sample holder having the sample rotating mechanism according to the third embodiment of the present invention. The sample holder includes a mechanism capable of rotating the needle-shaped sample 12 by a sample rotary shaft 54 in addition to a mechanism capable of translating a drive support portion 32 by rotating a micrometer 36. The sample rotary shaft 54 penetrates through the center of the sample holder 1. A knob 58 positioned at the center of the micrometer 36 is turned so that the rotary internal cylinder 51 of the sample base 11 attached to a holder leading end can be rotated. Accordingly, three-dimensional cubic processing can be performed in FIB processing. When viewed in an incident direction of an electron beam, information in a depth direction in the sample can be three-dimensionally acquired in TEM observation.

Note that, the present invention is not limited to the above embodiments, and includes various modifications. For example, the above embodiments have been described in detail in order to easily understand the present invention. The present invention is not necessarily limited to including all the configurations having been described above. Apart of the configuration in one of the embodiments can be replaced with the configuration in another embodiment. In addition, the configuration in one embodiment can be added to the configuration in another embodiment. With respect to a part of the configuration in each of the embodiments, additions, deletions, and replacements of the other configurations may be made.

REFERENCE SIGNS LIST

1 sample holder
2 atom probe device
3 charged particle beam device
11 sample base
12 needle-shaped sample
13 protrusion
14 male screw structure
15 sample holding portion
16 charged particle beam source
17 charged particle beam irradiation axis
21 housing
22 female screw structure
23 O-ring
31 cylindrical body
32 drive support portion
33 guide groove
34 hook portion
36 micrometer
42 housing holder
43a, 43b gate valve
44 sample exchanging rod
45 atom probe analyzing chamber
46 sample fixing portion for atom probe analysis
47 detector
48 sample exchanging chamber
49 preliminary discharging chamber
50 sample introducing rod
51 rotary internal cylinder
52 groove
53 external cylinder
54 sample rotary shaft
55 voltage source
56 atom
57 drawing position
58 knob

The invention claimed is:

1. A sample holder comprising:
a cylindrical body including one end open;
a sample base including a sample holding portion that holds a sample, at a leading end;
a drive support portion coupling to the sample base so as to be attachable and detachable, and configured to be movable in the body; and
a housing including a vacuum seal portion and an opening through which a charged particle beam to be irradiated to the sample held by the sample holding portion passes, enveloping the sample holding portion of the sample base at least partially, and coupling to the sample base or the drive support portion so as to be attachable and detachable,
wherein in a state where the drive support portion, the sample base, and the housing have been coupled to each other, the drive support portion is introduced into the body so that the vacuum seal portion of the housing comes in contact with the body and an airtight chamber is formed on a periphery of the sample holding portion.

2. The sample holder according to claim 1,
wherein a coupling manner between the sample base and the drive support portion and a coupling manner between the housing and the sample base or the drive support portion are different from each other.

3. The sample holder according to claim 1,
wherein the housing is coupled to the sample base so as to be attachable and detachable by rotation motion around an axis of the sample holder.

4. The sample holder according to claim 1,
wherein the housing is coupled to the drive support portion so as to be attachable and detachable by rotation motion around an axis of the sample holder.

5. The sample holder according to claim 1,
wherein the sample base includes an external cylinder and an internal cylinder that has the sample holding portion on the leading end and is axially rotatable inside the external cylinder, and has a rotating mechanism for axially rotating the internal cylinder with respect to the external cylinder.

6. An analytical vacuum device comprising:
a vacuum chamber;
a sample holder including:
a cylindrical body including one end open,
a sample base including a sample holding portion that holds a sample, at a leading end, a drive support portion coupling to the sample base so as to be attachable and detachable, and configured to be movable in the body, and a housing including a vacuum seal portion and an opening through which a charged particle beam to be irradiated to the sample held by the sample holding portion passes, enveloping the sample holding portion of the sample base at least partially, and coupling to the sample base or the drive support portion so as to be attachable and detachable, wherein in a state where the drive support portion, the sample base, and the housing have been coupled to each other, the drive support portion is introduced into the body so that the vacuum seal portion of the housing comes in contact with the body and an airtight chamber is formed on a periphery of the sample holding portion;

an attaching and detaching mechanism configured to couple the housing, the sample base, and the drive support portion to the sample holder in the vacuum chamber and configured to separate the housing, the sample base, and the drive support portion included in the body;

a sample fixing portion configured to receive the sample base that has held the sample in the vacuum chamber and has been separated by the attaching and detaching mechanism;

a mechanism configured to transfer and fix the sample base that has been separated by the attaching and detaching mechanism to the sample fixing portion; and a detector configured to analyze the sample held by the sample base fixed to the sample fixing portion.

7. The analytical vacuum device according to claim 6, wherein the attaching and detaching mechanism includes a housing holder that holds and evacuates the housing that has been separated from the sample holder to an evacuating position.

8. The analytical vacuum device according to claim 6, wherein the attaching and detaching mechanism includes a mechanism that separates the housing and the sample base.

9. The analytical vacuum device according to claim 6, wherein the attaching and detaching mechanism includes a mechanism that separates the housing from the drive support portion.

* * * * *